US012560799B2

(12) United States Patent
Rauniyar et al.

(10) Patent No.: US 12,560,799 B2
(45) Date of Patent: Feb. 24, 2026

(54) SCOPE MODIFICATIONS TO ENHANCE SCENE DEPTH INFERENCE

(71) Applicant: BOSTON SCIENTIFIC SCIMED, INC., Maple Grove, MN (US)

(72) Inventors: Niraj Prasad Rauniyar, Plymouth, MN (US); Robert J. Riker, Sewickley, PA (US); Longquan Chen, Andover, MA (US); Jeffrey A. Meganck, N Grafton, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 395 days.

(21) Appl. No.: 17/685,325

(22) Filed: Mar. 2, 2022

(65) Prior Publication Data

US 2022/0283425 A1    Sep. 8, 2022

Related U.S. Application Data

(60) Provisional application No. 63/155,988, filed on Mar. 3, 2021.

(51) Int. Cl.
*G02B 23/24* (2006.01)
*A61B 1/00* (2006.01)
(Continued)

(52) U.S. Cl.
CPC ...... *G02B 23/2484* (2013.01); *A61B 1/00009* (2013.01); *A61B 1/045* (2013.01);
(Continued)

(58) Field of Classification Search
CPC ............ G02B 23/2484; G02B 23/2469; A61B 1/00009; A61B 1/045; A61B 1/0638;
(Continued)

(56) References Cited

U.S. PATENT DOCUMENTS

| | | | |
|---|---|---|---|
| 5,061,995 A | 10/1991 | Lia et al. | |
| 5,693,003 A | 12/1997 | Woelfelschneider et al. | |

(Continued)

FOREIGN PATENT DOCUMENTS

| | | |
|---|---|---|
| CN | 100443041 C | 12/2008 |
| JP | H0313805 A | 1/1991 |

(Continued)

OTHER PUBLICATIONS

International Search Report and Written Opinion dated May 24, 2022 for International Application No. PCT/US2022/018576.
(Continued)

*Primary Examiner* — Michael J Carey
*Assistant Examiner* — Timothy Tuan Luu
(74) *Attorney, Agent, or Firm* — Seager, Tufte & Wickhem, LLP

(57) ABSTRACT

An imaging system and methods are presented for determining a size of a viewed object through a monocular endoscope. The system includes an imaging device mounted on the endoscope, at least one light source disposed in a fixed position relative to the imaging device, and a processor configured to receive input from the imaging device and analyze at least one of shadow effect from the light source, structured lighting provided by the light source, multi-point illumination including the light source, time-of-flight involving light pulses from the light source, and lateral color aberrations from the light source to determine the size of the viewed object.

20 Claims, 4 Drawing Sheets

(51) Int. Cl.

| | |
|---|---|
| *A61B 1/045* | (2006.01) |
| *A61B 1/06* | (2006.01) |
| *A61B 1/07* | (2006.01) |
| *A61B 1/307* | (2006.01) |
| *G01S 7/481* | (2006.01) |
| *G01S 7/4865* | (2020.01) |
| *G01S 17/89* | (2020.01) |
| *H04N 5/222* | (2006.01) |

(52) U.S. Cl.
CPC .......... *A61B 1/0638* (2013.01); *A61B 1/0655* (2022.02); *A61B 1/0676* (2013.01); *A61B 1/0684* (2013.01); *A61B 1/07* (2013.01); *G01S 7/4818* (2013.01); *G01S 7/4865* (2013.01); *G01S 17/89* (2013.01); *G02B 23/2469* (2013.01); *H04N 5/2226* (2013.01); *A61B 1/307* (2013.01)

(58) Field of Classification Search
CPC ... A61B 1/0655; A61B 1/0676; A61B 1/0684; A61B 1/07; A61B 1/307; A61B 5/0084; A61B 5/1076; A61B 1/00097; A61B 1/0605; A61B 1/00004; A61B 1/000094; G01S 7/4818; G01S 7/4865; G01S 17/89; H04N 5/2226
See application file for complete search history.

(56) References Cited

U.S. PATENT DOCUMENTS

| | | | |
|---|---|---|---|
| 8,696,546 | B2 | 4/2014 | Nicolaou et al. |
| 9,161,679 | B2 | 10/2015 | Christiansen et al. |
| 9,691,162 | B2 | 6/2017 | Christiansen |
| 9,737,232 | B2 | 8/2017 | Fan |
| 10,136,959 | B2 | 11/2018 | Mintz et al. |
| 10,258,415 | B2 | 4/2019 | Harrah et al. |
| 10,346,978 | B2 | 7/2019 | Wang et al. |
| 10,401,611 | B2 | 9/2019 | Stith et al. |
| 10,402,992 | B2 | 9/2019 | Wang et al. |
| 10,510,144 | B2 | 12/2019 | Zur |
| 10,531,074 | B2 | 1/2020 | Wilson et al. |
| 10,614,555 | B2 | 4/2020 | Fukazawa et al. |
| 10,694,933 | B2 | 6/2020 | Yamaguchi |
| 10,792,034 | B2 | 10/2020 | Scheib et al. |
| 2005/0254720 | A1 | 11/2005 | Tan et al. |
| 2013/0002844 | A1* | 1/2013 | Shida ............... A61B 1/000094 348/E7.085 |
| 2013/0079620 | A1 | 3/2013 | Kuth et al. |
| 2014/0336461 | A1 | 11/2014 | Reiter et al. |
| 2016/0338803 | A1 | 11/2016 | Pesach |
| 2017/0105613 | A1* | 4/2017 | Tsuruta ................ A61B 1/0625 |
| 2017/0237960 | A1* | 8/2017 | Kamm ................... H04N 23/56 348/46 |
| 2017/0360286 | A1* | 12/2017 | Kaku ................... A61B 1/0605 |
| 2018/0276877 | A1* | 9/2018 | Mountney ........ A61B 1/000095 |
| 2019/0051039 | A1 | 2/2019 | Tsuru et al. |
| 2020/0015925 | A1* | 1/2020 | Scheib ................ A61B 5/6844 |
| 2020/0100647 | A1 | 4/2020 | Craig et al. |
| 2020/0289230 | A1 | 9/2020 | Denlinger et al. |

FOREIGN PATENT DOCUMENTS

| | | |
|---|---|---|
| JP | 2005279028 A | 10/2005 |
| JP | 2016528972 A | 9/2016 |
| JP | 2016189859 A | 11/2016 |
| JP | 2016193144 A | 11/2016 |
| JP | 2017217215 A | 12/2017 |
| JP | 2018529404 A | 10/2018 |
| JP | 2020536698 A | 12/2020 |
| WO | 2012011187 A1 | 1/2012 |
| WO | WO-2020257701 A1 * 12/2020 ......... A61B 1/00006 |

OTHER PUBLICATIONS

Geng et al., "Review of 3-D Endoscopic Surface Imaging Techniques", IEEE Sensors Journal, 14(4): 945-960, Apr. 2014.

* cited by examiner

SCOPE MODIFICATIONS TO ENHANCE SCENE DEPTH INFERENCE

CROSS REFERENCE TO RELATED APPLICATIONS

This application claims the benefit of and priority to U.S. Provisional Patent Application Ser. No. 63/155,988 filed on Mar. 3, 2021, the disclosure of which is incorporated herein by reference.

TECHNICAL FIELD

The disclosure pertains to medical devices and more particularly to enhancements for depth determinations in endoscopy procedures, and methods for using such medical devices.

BACKGROUND

With any imaging system, users need to know the actual physical size of an object being displayed to accurately interpret the image. For optical imaging systems imaging a 2D scene at a fixed point in space, this is commonly achieved by calibrating the optical parameters of the system, such as focus length and distortion, and using information to compute a pixel size (frequently displayed using scale bars). This is not possible in monocular optical imaging systems that image a 3D scene with significant depth. In these systems, while the image sensor pixel size is fixed, the physical size of the object being displayed depends on the distance of that object from the collection optics. Two objects of identical size will appear to be different in the image; the object further from the optics will appear smaller.

This is a common problem in all endoscopy systems. It is particularly important to solve this problem for uretero-scopic procedures. Knowing the physical size of a kidney stone (and/or residual stone fragments) can directly impact procedural decision making and overall procedural effi-ciency. Optical calibration alone is not adequate in uretero-scopic applications between anatomical features and/or stone fragments will have a significant range of distances from the primary objective lens.

In current practice, the field of view size is estimated by intuitively comparing the object of known diameter (e.g. comparing size of stone to an adjacent laser fiber). It takes a significant amount of time for surgeons to develop this intuition. For endoscopic imaging systems, even this intu-ition is still limited. Endoscopes are inherently space result-ing in designs that (1) use a single objective lens and (2) rely on fixed focal length optics. These constraints result in imaging configurations where there is variable magnifica-tion of the object over the scene, and every pixel detected by the sensor may represent a different physical size on the object. This fundamental challenge requires more advanced designs to accurately measure size.

Methods and devices that provide size guidance during this crucial sizing step are needed to increase procedure efficacy, facilitate standardization of care, and improve patient safety.

SUMMARY

This disclosure provides design, material, manufacturing method, and use alternatives for medical devices. An example imaging system for determining a size of a viewed object, comprising a monocular endoscope, an imaging device mounted on the endoscope, at least one light source disposed in a fixed position relative to the imaging device, and a processor configured to receive input from the imaging device and analyze at least one of shadow effect from the light source, structured lighting provided by the light source, multi-point illumination including the light source, time-of-flight involving light pulses from the light source, and lateral color aberrations from the light source, wherein the analysis provides a depth determination for the viewed object from which a size of the object is inferred.

Alternatively or additionally to the embodiment above, the system further comprises a tool positionable relative to the imaging device and light source.

Alternatively or additionally to any of the embodiments above, the light source is spaced apart from the imaging device and the processor is configured to perform shadow effect analysis of a shadow cast from the tool.

Alternatively or additionally to any of the embodiments above, a reference point on the tool is positioned a first distance from the light source, wherein the shadow effect analysis includes determining a ratio of the first distance to a second distance from the light source to a surface on which a shadow of the tool is visible.

Alternatively or additionally to any of the embodiments above, a third distance from the light source to the object is determined and a fourth distance from the light source to a surface on which a shadow of the object is visible, wherein the processor is further configured to determine the size of the object based on the ratio.

Alternatively or additionally to any of the embodiments above, the at least one light source projects a predetermined light pattern onto the viewed object, and the processor is configured to perform structured lighting analysis by com-paring size and curvature of a measured pattern on the object with the predetermined light pattern and determine the size of the object based on the comparison.

Alternatively or additionally to any of the embodiments above, the at least one light source projecting a light pattern includes an optical fiber positioned between the endoscope and the object.

Alternatively or additionally to any of the embodiments above, the optical fiber includes a first optical fiber providing uniform illumination and a second optical fiber providing the predetermined light pattern.

Alternatively or additionally to any of the embodiments above, the at least one light source includes at least first and second light sources that are separately controlled.

Alternatively or additionally to any of the embodiments above, the first and second light sources provide different color light.

Alternatively or additionally to any of the embodiments above, the system further comprises a third light source, wherein the first, second, and third light sources are sepa-rately controlled red, green, and blue LEDs.

Alternatively or additionally to any of the embodiments above, the system further comprises a time-of-flight sensor, wherein the at least one light source is configured to emit light pulses.

Alternatively or additionally to any of the embodiments above, the sensor and light source are disposed through the endoscope and extend distally of a distal end of the endo-scope.

Alternatively or additionally to any of the embodiments above, the light source includes a lateral color aberration over a wavelength range being detected by the imaging device, wherein the processor is configured to measure wavelength shift and correlate it with distance to the object.

An example method of determining the size of an object viewed through a monocular endoscope comprises capturing an image of the object using an imaging device mounted on the endoscope and using at least one light source disposed in a fixed position relative to the imaging device, analyzing the image with a processor configured to perform one or more of shadow effect analysis, structured light analysis, multi-point illumination analysis, time-of-flight analysis, and later color aberration analysis, and determining the size of the object based on the one or more analyses.

Alternatively or additionally to any of the embodiments above, the analysis is shadow effect, the method further comprising positioning a tool of known size through the endoscope to a first distance and illuminating the tool with the at least one light source to create a shadow of the tool and measuring a second distance from the at least one light source to a surface on which the shadow of the tool is visible, wherein the shadow effect analysis includes determining a ratio of the first distance to the second distance and using the ratio to determine the size of the object based on a third distance measured to the object and a fourth distance to the object's shadow.

Alternatively or additionally to any of the embodiments above, the analysis is a structured light analysis, the method further comprising projecting a predetermined light pattern onto the imaged field including the object using the at least one light source and measuring a resulting pattern on the object, and the structured lighting analysis includes comparing size and curvature of a measured pattern on the object with the predetermined light pattern and determine the size of the object based on the comparison.

Alternatively or additionally to any of the embodiments above, the analysis is a multi-point illumination analysis, the at least one light source including at least first and second light sources that are separately controlled, method further comprising separately illuminating the object with the first and second light sources.

Alternatively or additionally to any of the embodiments above, the analysis includes time-of-flight analysis, wherein the at least one light source is configured to emit discrete light pulses, wherein the endoscope further comprises a time-of-flight sensor.

Alternatively or additionally to any of the embodiments above, the analysis includes leveraged optical aberration analysis, wherein the at least one light source includes a lateral color aberration over a wavelength range that is detected by the imaging device, wherein analyzing the image includes measuring wavelength shift and correlating it with distance to the object.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
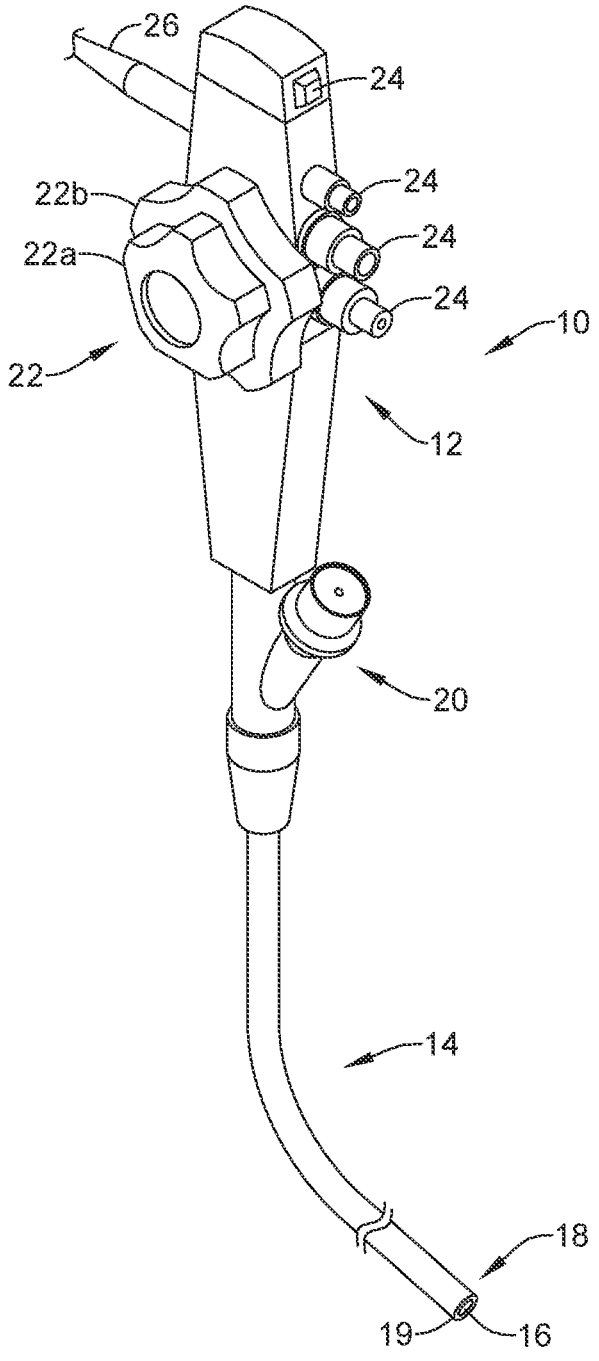
FIG. 1 is a perspective view of an example endoscope assembly.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5). Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The detailed description is intended to illustrate but not limit the disclosure. Those skilled in the art will recognize that the various elements described may be arranged in various combinations and configurations without departing from the scope of the disclosure. The detailed description illustrates example embodiments of the disclosure.

The current ureteroscopic systems are monocular, and so are lacking in direct data related to the depth of objects in the scene. Some systems estimate the size of objects by overlaying a simple grid onto the image displayed on screen, and using the grid size to estimate the size of the object. However, such analysis does not take into account the depth of the object from the light source and imaging device. Even when objects of known size in the field of view are used to create the size grid, depth remains an unknown variable that may greatly alter the viewed size of the object compared to the grid. For example, a stone positioned 5 mm distal of the light source and imaging device may appear significantly smaller than a similar sized stone positioned 1 mm from the light source and imaging device. The grid applied to the image on the screen may make the two stones appear to be of different size when in reality they are the same physical size.

An example endoscope assembly 10 is illustrated in FIG. 1. Endoscope 10 may be any of a number of types of endoscopes or related medical devices usually identified by the particular anatomy desired to be reached. For example, endoscope 10 may be a bronchoscope, colonoscope, duodenoscope, esophagoscope, guide tubes, introducers (without or without vision or visualization capabilities), or any other type of endoscope or related medical device. Endoscope 10 may include a handpiece 12 and an elongate shaft 14 extending distally from handpiece 12 to a distal tip 18. Shaft 14 may include a lumen defining a working channel 16 extending through shaft 14 from a distal end 19 near distal tip 18 of shaft 14 to an access port 20 that may be positioned in handpiece 12 or another portion of endoscope 10. Although endoscope 10 is depicted with a single working channel 16 in FIG. 1, it can be appreciated that in other embodiments, endoscope 10 may include multiple working channels, as desired. The working channel(s) may be configured for the passage of a variety of surgical equipment, including, but not limited to, imaging devices and tools for irrigation, vacuum suctioning, biopsies, and drug delivery.

Handpiece 12 may include one or a plurality of controls 22, such as rotating knobs, which may be used to control movement of distal tip 18 of shaft 14 during operation. For example, a first rotating knob 22a may control up and down movement or deflection of distal tip 18 of shaft 14, while a second rotating knob 22b may control side-to-side movement or deflection of distal tip 18 of shaft 14. Handpiece 12 may also include one or a plurality of buttons 24, which may be used to activate suction or deliver fluid such as air, saline and/or water, etc. through a lumen of the endoscope 10 or perform other functions as desired. Additionally, handpiece 12 may include an optical cable 26 connected to an external light source (not shown).

Figure 2:
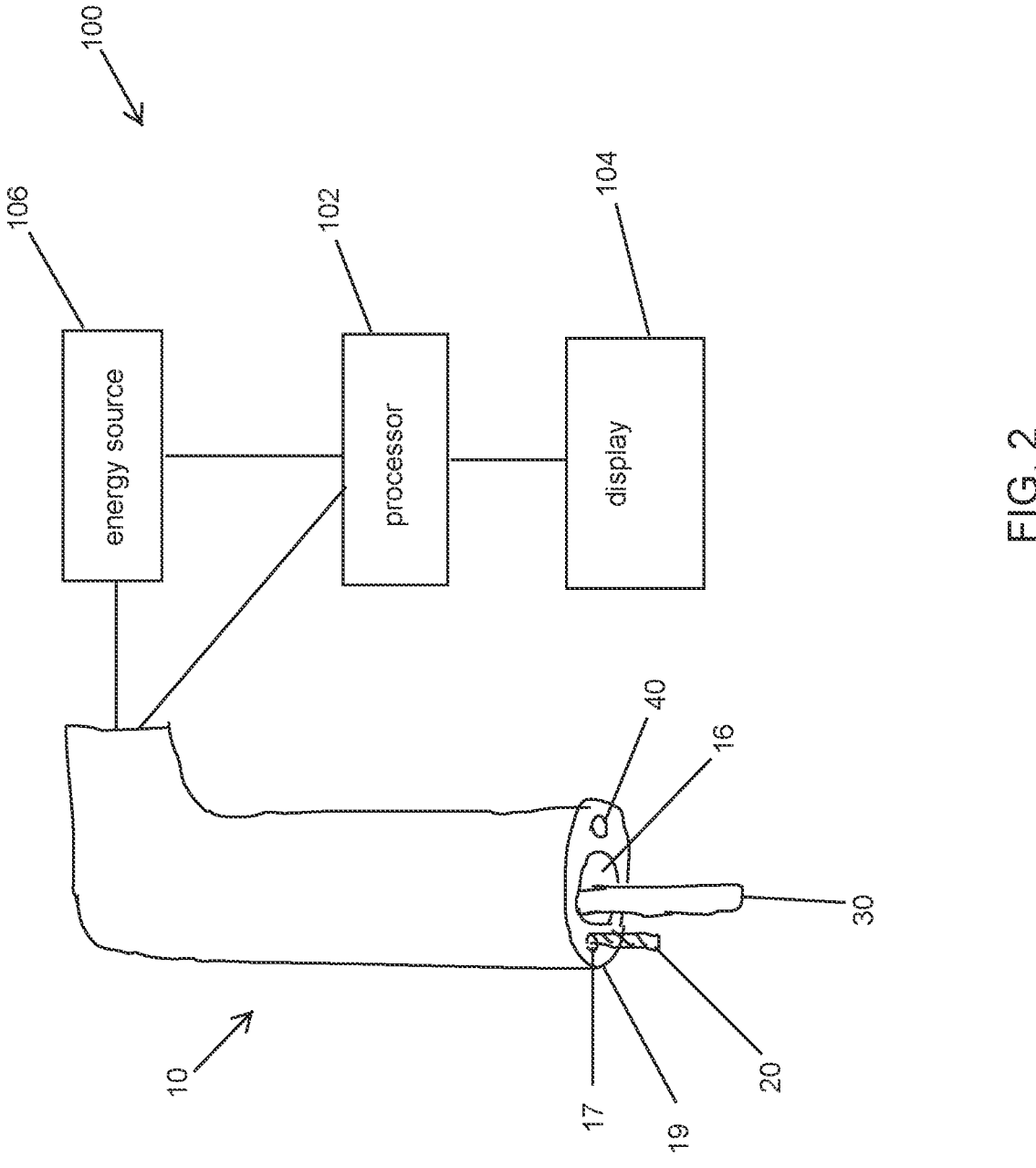
FIG. 2 is a schematic view of a system for determining the size of an object according to one example of the present disclosure.

FIG. 2 illustrates a system 100 for determining the size of an object according to one example of the present disclosure. The system may include a processor 102 that is operatively coupled to a display 104. The processor 102 may also be coupled to an energy source 106 and the endoscope 10. The processor 102 may be generally configured to accept information from the system and system components, and process the information according to various algorithms. The energy source 108 may include an optical energy source, such as, e.g., a holmium (Ho) laser source, a carbon dioxide ($CO_2$) laser source, an Argon laser source, a diode laser source, or another suitable laser source. In some examples, one or more high power LED may be used in place of a laser source. In some examples, an intense, pulsed light source may be used in place of a laser source. The optical energy source may be mounted at the distal end 19 of the endoscope 10, or on a catheter or other suitable elongate member.

In some examples, one or more optical fibers 20 may extend from the distal end 19 of the endoscope 10 through a lumen 17 and be configured to deliver light energy from the energy source 106 to a treatment location. In other examples, the optical fiber 20 be fixed at the distal end 19. An imaging device 40 may also be disposed at the distal end 19 of the endoscope 10. The imaging device 40 may include any suitable device configured to provide images to the processor 102 for display on the display 104 including, e.g., a CMOS imaging sensor or other solid-state device or camera and one or more glass or polymeric lenses that produce electronic image signals representative of an image of the tissue or other objects in front of the imaging device 40. The imaging device 40 may be a low light sensitive, low noise video VGA, CMOS, color imager or higher resolution sensor such as SVGA, SXGA, or XGA. In some examples, the imaging device 40 and/or the light source may be fixed relative to one another.

Depth data is available in stereoscopic systems that provide multiple views of the same scene from a different perspective, separated by a known distance. However, a monocular endoscope may not automatically provide depth of scene. Five techniques may be used to enhance monocular depth estimates and provide distance data analogous to stereoscopic systems: shadow analysis, structured lighting, multi-point illumination, a time-of-flight sensor, and leveraged optical aberrations.

Shadow Analysis

In shadow analysis it is acknowledged that the source of scene illumination, while very close to the imaging device, does not exactly coincide, as shown in FIG. 2. When the illumination source remains in a fixed position relative to the imaging device, distances to an object of known size and its shadow may be used in the analysis. In particular, a distance D1 may be measured from the source of illumination to an object of known size and/or depth within the viewed field, and a distance D2 may be measured from the source of illumination to the surface on which the object's shadow is visible. A shadowing effect may be expected to be proportional to the ratio of D1/D2. The depth of the shadow position can then be directly calculated. As the dimensions of the tool are known, the part of the tool (reference point) casting the shadow may be inferred, and the depth of that part within the field can be measured, and the size inferred.

A reference point or known part of a tool is positioned a first distance D1 from the light source, and then D2 is measured to the surface on which the tool's shadow is seen. The ratio of D1/D2 is calculated. This ratio of D1/D2 provides a depth estimate that may be used to calculate the size of an unknown object in the field of view. The distances D1 and D2 are measured for the unknown object and the ratio is calculated and used to estimate the size of the unknown object. A third distance from the light source to the unknown object is determined and a fourth distance from the light source to a surface on which a shadow of the unknown object is visible, and the system's processor determines the size of the unknown object based on the ratio.

Figure 3:
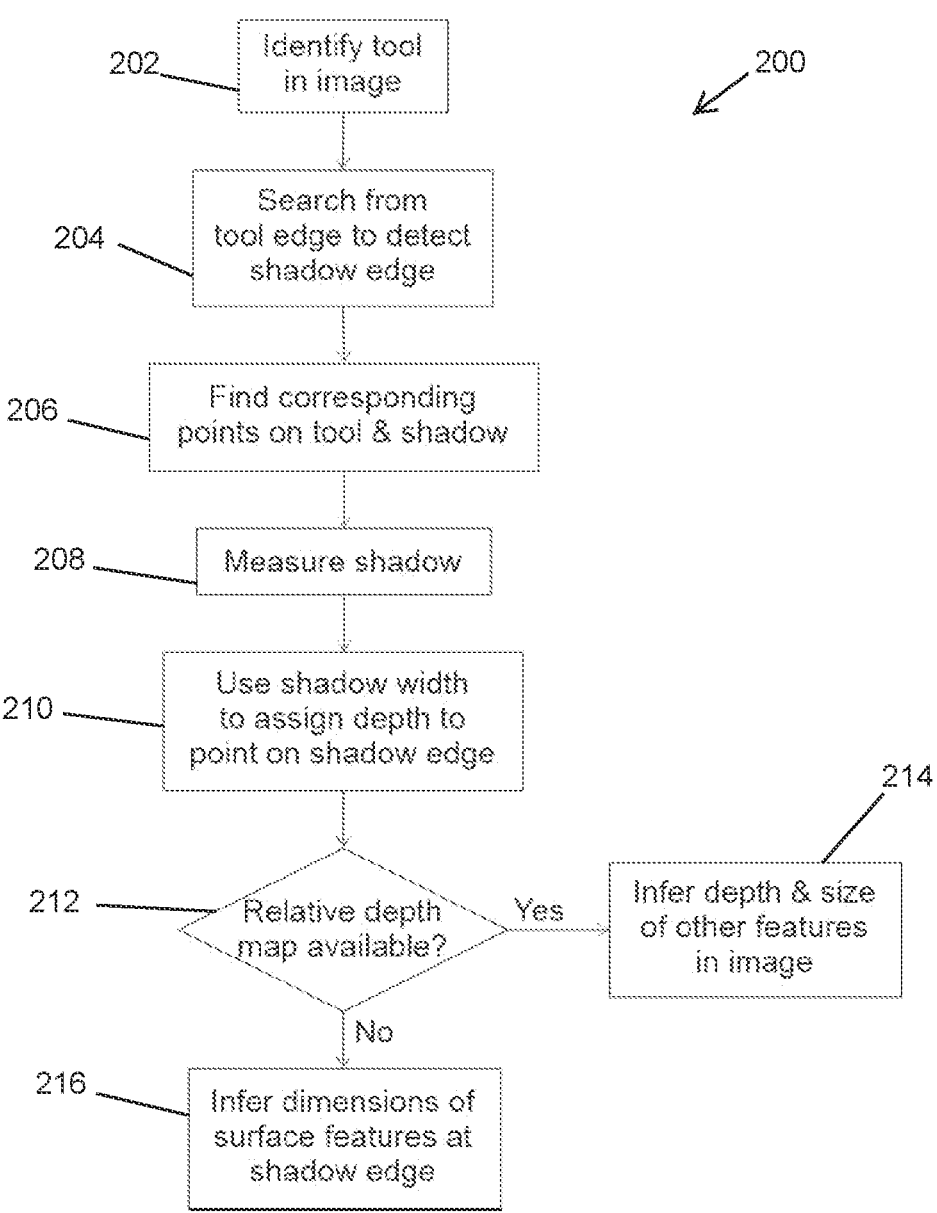
FIG. 3 is a flow diagram of a method of determining the size of an object viewed through an endoscope using shadow analysis.

One method 200 of determining the size of an object viewed through a monocular endoscope is illustrated in FIG. 3. An object of known size, such as a tool, may be placed at a known depth relative to the endoscope, e.g., the edge of a tool in the working channel. The tool is identified in the image provided by the imaging device (step 202). Next, the user searches from the tool edge to detect a shadow edge cast from the tool onto a tissue surface (step 204). Corresponding points on the tool and shadow are found (step 206), and the shadow is measured (step 208). The width of the shadow is used to assign depth to a point on the shadow edge (step 210). If a relative depth map is available (step 212), then the depth, size and other features of the image are inferred (step 214). If no relative depth map is available, the dimensions of surface features at the shadow edge are inferred (step 216).

In order to convert information about the depth of a tool shadow to the depth (and therefore size) of an object such as a kidney stone, the relative depths within the scene may be established through means such as epipolar measurements using successive, registered images and other lighting cues. These techniques may yield a depth map for a scene, but without any absolute scale, so a first reference point may be determined to be twice as far away from a light source as a second reference point, but without an accurate way to determine if the points are 4 and 2 mm away, or 8 and 4 mm, or any such combination. By reliably measuring the depth of a single point in the scene that is also in the relative depth map, the scale may be determined, and absolute distances and sizes may be inferred for every other feature in the depth map.

In some examples, the tool may have markings such as incremental measurement markings or a geometric pattern that may be used to determine D1. See, for example, U.S. Provisional Application No. 63/155,939, titled "Measurement Markings in Distal Tip Imaging Field of View" filed on Mar. 3, 2021, the entirety of which is incorporated by reference.

Use of tool shadows also maximizes the ratio of depths by virtue of the tool's proximity to the light source, thereby maximizing the signal to noise ratio (SNR) of the depth estimates. Some shadows may be barely detectable, and may benefit from estimation at a sub-pixel resolution, such that image processing techniques may be employed to improve penumbra estimates, including multi-frame sampling with registration.

Structured Lighting

Structured lighting techniques are known in optical measurement measurements, and often include the projection of known patterns or gratings into the imaged field, where the pattern is projected from a position at a known offset from the imaging device recording the scene, thereby creating a stereoscopic baseline. Distance and topography can be calculated by comparing the size and curvature of measured patterns in comparison to the known patterns.

Figure 4:
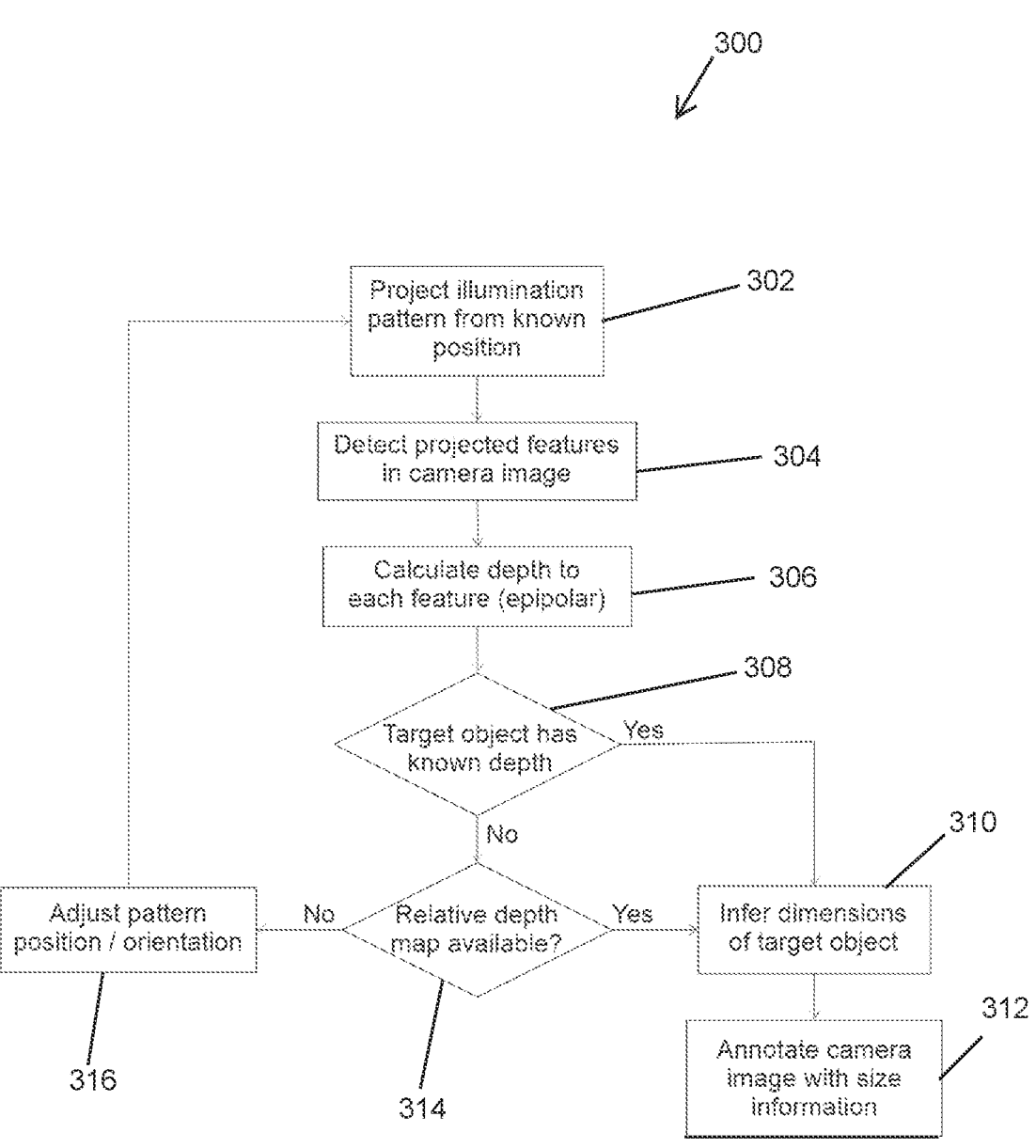
FIG. 4 is a flow diagram of a method of determining the size of an object viewed through an endoscope using structured lighting analysis.

One method 300 of determining the dimensions of a target object are illustrated in FIG. 4. In step 302, an illumination pattern from a known position is projected onto the target object. In step 304, projected features in the camera image are detected. In step 306, the depth to each feature (epipolar) is calculated. In step 308, whether or not the target object has a known depth is determined. If yes, the dimensions of the target object are inferred (step 310), and then the camera image is annotated with size information (step 312). If the target object does not have a known depth (step 308), then the next question is whether or not a relative depth map is available (step 314). If yes, then the method proceeds to step 310. If no, then the pattern position and/or orientation is adjusted (step 316) and the method returns to step 302.

This approach presents unique challenges in ureteroscopy, wherein both the lighting and imaging device systems are tightly constrained and very close. The optics necessary to project an identifiable pattern may be impractical to incorporate directly into the ureteroscope. Therefore, an additional tool that can be interposed between the scope and the scene, potentially through the scope working channel, may serve to create recognizable lighting patterns that indicate depth, as with the shadow analysis above. For example, an optical fiber may be used as the additional tool to project a predetermined, recognizable lighting pattern onto the field of view. The system processor than performs structured lighting analysis by comparing the size and curvature of the pattern measured on the unknown object with the predetermined light pattern and determines the size of the unknown object based on the comparison. In some examples, first and second optical fibers may be used to provide the predetermined light pattern.

In another example, lights with two known wavelengths disposed at a known separation distance from the imaging device may act as a source of structured lighting. Two or more light-emitting diodes (LEDs) of the same or different wavelength or an LED with the aiming beam of the laser, or a pilot burst of the laser may be used. In a further example, two optical fibers may be used, a first with uniform illumination for standard visualization and a second with structured light for physical depth measurements, where illumination is generated within the scope itself. When multiple LEDs or optical fibers are used, they may be separately and individually controlled. In particular with LEDs, turning them on an off separately may provide the user with the ability to change the color of light by mixing light from different color LEDs to achieve a desired light color.

Multi-Point Illumination

In conjunction with either or both techniques above, a second, separately controllable lighting source may be incorporated on the scope, with maximal practical source separation, that will provide additional depth information. The above-described shadow effect may be determined for each light source. Differentiation of the shadows from the different light sources may be achieved through timing (by toggling the sources on and off, potentially at intervals synchronized to the camera frame rate), or through color, e.g., using complementary red-blue light sources may create detectable color fringes in the image, measurement of which would permit depth inference. Likewise, individual red, green and blue (RGB) LEDs, such as micro-LEDs, on the scope tip may create balanced lighting with subtle depth cues that a computer may be able to interpret without distracting the user. For example, white light may be achieved by combining the output of the red, green, and blue LEDs.

Time-of-Flight Sensor

The time-of-flight principle is a method for measuring the distance between a sensor and an object, and is based on the time difference between the emission of a light signal and its return to the sensor, after being reflected by the object. A time-of-flight sensor requires a light source that can emit light pulses, which can be provided by a laser or an LED. The system may either modify the current LED or leverage the lithotripsy system to generate light pulses. Instead of mounting the sensor onto the scope, the sensor and light sources may be interposed between the scope and the scene. In this manner, the sensor and light sources may be extended distally beyond the distal end of the scope.

Leverage Optical Aberrations

Endoscopy imaging sensors may use RGB patterns in a tiled (typically Bayer) layout. These adjacent portions of the sensor are then recomposed into a single pixel representing a single co-located position in (RGB) color. This typically works quite well, particularly if the optics are designed to minimize lateral color aberrations that can result in ray shift within the image plane. However, the optics may instead be designed to deliberately include lateral color aberration over the wavelength range being detected. The ray shift at the individual red, green, and blue sensors in the raw image may be measurable and may be correlated to physical distances. The color aberration may be based on the material used for the lens. In some examples, Flint glass may be used. Flint glass has some lead and a particular high chromatic aberration (described by an Abbe number below 50), and high refractive index (usually above 1.55). Some types of flint glass are: F, LF, SF, KF, BaF, BaLF. Lead-free flint glass usually has a "N" before their name. For example, N-SF8. If the shifts are significant relative to the pixel size, this may show up in the raw pixels. If paired with a glass grade that has differential absorption in this portion of the visible spectrum (e.g. N-SF57), and/or paired with collimated multispectral illumination, individual R, G and B images could conceivably be created, registered, and used to estimate some difference in distances.

One or more of the above techniques may be used in an imaging system to provide a more accurate estimate of the physical size of an object viewed through a monocular endoscope. The imaging system may include a monocular endoscope, an imaging device mounted on the endoscope, at least one light source disposed in a fixed position relative to the imaging device, and a processor configured to receive input from the imaging device and analyze one or more of shadow effect from the light source, structured lighting provided by the light source, multi-point illumination including the light source, time-of-flight involving light pulses from the light source, and lateral color aberrations from the light source. The analysis provides a size determination for the viewed object.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:
1. An imaging system for determining a size of a viewed object, comprising:
   a monocular endoscope;
   an imaging device mounted on the endoscope;
   at least one light source disposed in a fixed position relative to the imaging device;
   a tool positionable relative to the imaging device and the at least one light source; and
   a processor configured to receive input from the imaging device of a field of view and analyze a shadow effect from the light source, and one or more of structured lighting provided by the light source, multi-point illumination including the light source, time-of-flight involving light pulses from the light source, and lateral color aberrations from the light source;
   wherein the analysis provides a depth determination for the viewed object in the field of view from which a size of the object is inferred;
   wherein the light source is spaced apart from the imaging device and the processor is configured to perform the shadow effect analysis of a shadow cast from the tool;
   wherein a first distance is defined as a distance between a reference point on the tool and the light source, wherein the shadow effect analysis includes determining a ratio of the first distance to a second distance from the light source to a surface on which a shadow of the tool is visible; and
   wherein the processor is further configured to algorithmically combine results from the shadow effect from the light source and one or more of structured lighting provided by the light source, multi-point illumination including the light source, time-of-flight involving light pulses from the light source, and lateral color aberrations from the light source to generate a composite depth map that integrates depth information from the results.

2. The system of claim 1, wherein a third distance from the light source to the object is determined and a fourth distance from the light source to a surface on which a shadow of the object is visible, wherein the processor is further configured to use the ratio of the first distance to the second distance to determine the size of the object based on the third distance and the fourth distance.

3. The system of claim 1, wherein the at least one light source projects a predetermined light pattern onto the viewed object, and the processor is configured to perform structured lighting analysis by comparing size and curvature of a measured pattern on the object with the predetermined light pattern and determine the size of the object based on the comparison.

4. The system of claim 3, wherein the at least one light source projecting a light pattern includes an optical fiber positioned between the endoscope and the object.

5. The system of claim 4, wherein the optical fiber includes a first optical fiber providing uniform illumination and a second optical fiber providing the predetermined light pattern.

6. The system of claim 1, wherein the at least one light source includes at least first and second light sources that are separately controlled.

7. The system of claim 6, wherein the first and second light sources provide different color light.

8. The system of claim 7, further comprising a third light source, wherein the first, second, and third light sources are separately controlled red, green, and blue LEDs.

9. The system of claim 1, further comprising a time-of-flight sensor, wherein the at least one light source is configured to emit light pulses.

10. The system of claim 9, wherein the sensor and light source are disposed through the endoscope and extend distally of a distal end of the endoscope.

11. The system of claim 1, wherein the light source includes a lateral color aberration over a wavelength range being detected by the imaging device, wherein the processor is configured to measure wavelength shift and correlate it with distance to the object.

12. A method of determining the size of an object viewed through a monocular endoscope, comprising:

capturing an image of the object using an imaging device mounted on the endoscope and using at least one light source disposed in a fixed position relative to the imaging device and a tool positionable relative to the imaging device and the at least one light source;

analyzing the image with a processor configured to perform a shadow effect analysis and one or more of structured light analysis, multi-point illumination analysis, time-of-flight analysis, and later color aberration analysis;

algorithmically combining results from the shadow effect analysis and one or more of structured light analysis, multi-point illumination analysis, time-of-flight analysis, and lateral color aberration analysis to generate a composite depth map that integrates depth information from the analyses; and determining the size of the object based on the composite depth map;

wherein the light source is spaced apart from the imaging device and the processor is configured to perform the shadow effect analysis of a shadow cast from the tool; and wherein a reference point on the tool is positioned a first distance from the light source, wherein the shadow effect analysis includes determining a ratio of the first distance to a second distance from the light source to a surface on which a shadow of the tool is visible.

13. The method of claim 12, wherein the analysis is a structured light analysis and shadow effect analysis, the method further comprising projecting a predetermined light pattern onto the imaged field including the object using the at least one light source and measuring a resulting pattern on the object, and the structured lighting analysis includes comparing size and curvature of a measured pattern on the object with the predetermined light pattern and determine the size of the object based on the comparison.

14. The method of claim 12, wherein the analysis is a multi-point illumination analysis and shadow effect analysis, the at least one light source including at least first and second light sources that are separately controlled, the method further comprising separately illuminating the object with the first and second light sources.

15. The method of claim 12, wherein the analysis includes time-of-flight analysis, wherein the at least one light source is configured to emit discrete light pulses, wherein the endoscope further comprises a time-of-flight sensor.

16. The method of claim 12, wherein the analysis includes leveraged optical aberration analysis, wherein the at least one light source includes a lateral color aberration over a wavelength range that is detected by the imaging device, wherein analyzing the image includes measuring wavelength shift and correlating it with distance to the object.

17. An imaging system for determining a size of a viewed object, comprising:

a monocular endoscope;

an imaging device mounted on the endoscope;

at least one light source disposed in a fixed position relative to the imaging device;

a tool positionable relative to the imaging device and the at least one light source; and a processor configured to receive input from the imaging device of a field of view and analyze shadow effect from the light source, and one or more of structured lighting provided by the light source, multi-point illumination including the light source, time-of-flight involving light pulses from the light source, and lateral color aberrations from the light source;

wherein the analysis provides a depth determination for the viewed object in the field of view from which a size of the object is inferred; wherein the light source is spaced apart from the imaging device and the processor is configured to perform shadow effect analysis of a shadow cast from the tool;

wherein a first distance is defined as a distance between a reference point on the tool and the light source, wherein the shadow effect analysis includes determining a ratio of the first distance to a second distance from the light source to a surface on which a shadow of the tool is visible.

18. The system of claim 17, wherein a third distance from the light source to the object is determined and a fourth distance from the light source to a surface on which a shadow of the object is visible, wherein the processor is further configured to use the ratio of the first distance to the second distance to determine the size of the object based on the third distance and the fourth distance.

19. The system of claim 17, wherein the at least one light source projects a predetermined light pattern onto the viewed object, and the processor is configured to perform structured lighting analysis by comparing size and curvature of a measured pattern on the object with the predetermined light pattern and determine the size of the object based on the comparison.

20. The system of claim 17, wherein the sensor and the at least one light source are disposed through the endoscope and extend distally of a distal end of the endoscope.

* * * * *